US00PP21944P2

(12) United States Plant Patent
Miyazaki

(10) Patent No.: US PP21,944 P2
(45) Date of Patent: May 31, 2011

(54) *PHLOX* PLANT NAMED 'SUNPHLOCOPAPI'

(50) Latin Name: *Phlox drummondii*
Varietal Denomination: Sunphlocopapi

(75) Inventor: Kiyoshi Miyazaki, Shiga (JP)

(73) Assignee: Suntory Flowers Ltd., Tokyo (JP)

( * ) Notice: Subject to any disclaimer, the term of this patent is extended or adjusted under 35 U.S.C. 154(b) by 0 days.

(21) Appl. No.: 12/658,730

(22) Filed: Feb. 12, 2010

(51) Int. Cl.
*A01H 5/00* (2006.01)

(52) U.S. Cl. ..... Plt./320

(58) Field of Classification Search ..... Plt./320
See application file for complete search history.

*Primary Examiner* — Kent L Bell
(74) *Attorney, Agent, or Firm* — C. A. Whealy

(57) ABSTRACT

A new and distinct cultivar of *Phlox* plant named 'Sunphlocopapi', characterized by its compact and mounding plant habit; vigorous growth habit; freely branching and flowering habit; long flowering period; light red purple-colored flowers with red purple-colored centers; and good garden performance.

1 Drawing Sheet

Botanical designation: *Phlox drummondii.*
Cultivar denomination: 'SUNPHLOCOPAPI'.

BACKGROUND OF THE INVENTION

The present invention relates to a new and distinct cultivar of *Phlox* plant, botanically known as *Phlox drummondii* and hereinafter referred to by the name 'Sunphlocopapi'.

The new *Phlox* plant is a product of a planned breeding program conducted by the Inventor in Higashiomi, Shiga, Japan. The objective of the breeding program was to create new compact, mounding and freely branching *Phlox* plants with attractive flower coloration.

The new *Phlox* plant originated from a cross-pollination made by the Inventor in April, 2004, in Higashiomi, Shiga, Japan, of a proprietary selection of *Phlox drummondii* identified as code number 2Ph-26c, not patented, as the female, or seed, parent with a proprietary selection of *Phlox drummondii* identified as code number 0Ph-18-M, not patented, as the male, or pollen, parent. The new *Phlox* plant was discovered and selected by the Inventor as a single flowering plant within the progeny of the stated cross-pollination in a controlled greenhouse environment in Higashiomi, Shiga, Japan in May, 2005.

Asexual reproduction of the new *Phlox* plant by cuttings in a controlled greenhouse environment in Higashiomi, Shiga, Japan since June, 2005, has shown that the unique features of this new *Phlox* plant are stable and reproduced true to type in successive generations.

SUMMARY OF THE INVENTION

Plants of the new *Phlox* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Sunphlocopapi'. These characteristics in combination distinguish 'Sunphlocopapi' as a new and distinct cultivar of *Phlox:*

1. Compact and mounding plant habit.
2. Vigorous growth habit.

3. Freely branching and flowering habit.
4. Long flowering period.
5. Light red purple-colored flowers with red purple-colored centers.
6. Good garden performance.

Plants of the new *Phlox* differ from plants of the female parent selection primarily in flower color as plants of the female parent selection have white-colored flowers. In addition, plants of the new *Phlox* are not as compact as plants of the female parent selection.

Plants of the new *Phlox* differ from plants of the male parent selection primarily in flower color as plants of the male parent selection have salmon pink-colored flowers. In addition, plants of the new *Phlox* are smaller than plants of the male parent selection.

Plants of the new *Phlox* can also be compared to plants of *Phlox drummondii* 'Sunphlopin', disclosed in U.S. Plant Pat. No. 16,361. In side-by-side comparisons conducted in Higashiomi, Shiga, Japan, plants of the new *Phlox* and 'Sunphlopin' differed in the following characteristics:

1. Plants of the new *Phlox* were smaller than plants of 'Sunphlopin'.
2. Plants of the new *Phlox* had slightly shorter internodes than plants of 'Sunphlopin'.
3. Plants of the new *Phlox* and 'Sunphlopin' differed in flower color.

BRIEF DESCRIPTION OF THE PHOTOGRAPHS

The accompanying colored photographs illustrate the overall appearance of the new *Phlox* plant, showing the colors as true as it is reasonably possible to obtain in colored reproductions of this type. Colors in the photographs may differ slightly from the color values cited in the detailed botanical description which accurately describe the colors of the new *Phlox* plant.

The photograph at the top of the sheet comprises a side perspective view of a typical flowering plant of 'Sunphlocopapi' grown in a container.

The photograph at the bottom of the sheet is a close-up view of typical flowers and leaves of 'Sunphlocopapi'.

DETAILED BOTANICAL DESCRIPTION

The aforementioned photographs and following observations, measurements and values describe plants grown 15-cm containers in Higashiomi, Shiga, Japan, under commercial practice during the early summer in an outdoor nursery with day temperatures averaging 23° C. and night temperatures averaging 13° C. Plants were five and six months old when the description and photographs, respectively, were taken. In the following description, color references are made to The Royal Horticultural Society Colour Chart, 2001 Edition, except where general terms of ordinary dictionary significance are used.

Botanical classification: *Phlox drummondii* 'Sunphlocopapi'.

Parentage:

*Female, or seed, parent.*—Proprietary selection of *Phlox drummondii* identified as code number 2Ph-26c, not patented.

*Male, or pollen, parent.*—Proprietary selection of *Phlox drummondii* identified as code number 0Ph-18-M, not patented.

Propagation:

*Type.*—By cuttings.

*Time to initiate roots.*—About two to three weeks at 20° C. to 25° C.

*Time to produce a rooted young plant.*—About one to two months at 20° C. to 25° C.

*Root description.*—Fibrous; white in color.

*Rooting habit.*—Freely branching; moderately dense.

Plant description:

*Plant and growth habit.*—Compact and mounding plant habit; vigorous growth habit; freely branching habit with lateral branches potentially developing at every node; pinching enhances lateral branch development.

*Plant height.*—About 17.1 cm.

*Plant width (spread).*—About 28.9 cm.

*Lateral branches.*—Length: About 16.1 cm. Diameter: About 2.2 mm. Internode length: About 1.1 cm. Strength: Strong. Texture: Pubescent. Color: Close to 144B.

Foliage description:

*Arrangement.*—Alternate, simple; sessile.

*Length.*—About 3.2 cm.

*Width.*—About 1.3 cm.

*Shape.*—Narrowly elliptic.

*Apex.*—Acute.

*Base.*—Obtuse.

*Margin.*—Entire.

*Texture, upper and lower surfaces.*—Pubescent.

*Venation pattern.*—Pinnate, reticulate.

*Color.*—Developing and fully expanded leaves, upper surface: Close to 137C; venation, close to 145A. Developing and fully expanded leaves, lower surface: Close to 144A; venation, close to 145A.

Flower description:

*Flower arrangement and habit.*—Single rotate flowers arranged in terminal and axillary cymes; flowers face mostly upright; cymes roughly hemispherical in shape; freely flowering habit with about 58 flowers per plant.

*Fragrance.*—None detected.

*Natural flowering season.*—Plants begin flowering about two months after planting; plants flower continuously from spring to autumn in Japan.

*Postproduction longevity.*—Flowers last about five days on the plant; flowers not persistent.

*Flower buds.*—Height: About 1.72 cm. Diameter: About 3.1 mm. Shape: Clavate. Color: Close to 75B.

*Inflorescence height.*—About 2.9 cm.

*Inflorescence diameter.*—About 5.5 cm.

*Flower diameter.*—About 2.8 cm.

*Flower depth.*—About 1.5 cm.

*Tube length.*—About 1.3 cm.

*Tube diameter, base.*—About 2 mm.

*Petals.*—Quantity per flower: Typically five in a single whorl; petals fused at the base into a narrow tube. Length: About 1.45 cm. Lobe width: About 1.28 cm. Shape: Broadly rhombic. Apex: Obtuse. Margin: Entire. Texture, upper and lower surfaces and throat: Smooth, glabrous. Texture, tube: Pubescent. Color: Developing and fully expanded petals, upper surface: Close to 73A; towards the center, close to 75D; central star, close to 61B. Developing and fully expanded petals, lower surface: Close to 75D. Throat: Close to 186A. Tube: Close to 177D.

*Sepals.*—Quantity per flower: Typically five in a single whorl, fused towards the base; calyx star-shaped. Length: About 4.5 mm. Width: About 1.3 mm. Shape: Lanceolate. Apex: Acute. Margin: Entire. Texture, upper and lower surfaces: Smooth, glabrous. Color, developing and fully expanded sepals, upper surface: Close to 137C. Color, developing and fully expanded sepals, lower surface: Close to 137C.

*Peduncles.*—Length: About 2.1 mm. Diameter: About 1.5 mm. Strength: Strong. Texture: Pubescent. Color: Close to 144A.

*Pedicels.*—Length: About 5.1 mm. Diameter: About 0.7 mm. Strength: Strong. Texture: Pubescent. Color: Close to 144A.

*Reproductive organs.*—Stamens: Quantity per flower: Typically five. Stamen length: About 5 mm to 12 mm. Anther shape: Lanceolate. Anther size: About 2 mm by 0.9 mm. Anther color: Close to 12A. Pollen amount: Moderate. Pollen color: Close to 12A. Pistils: Quantity per flower: One. Pistil length: About 3.7 mm. Stigma shape: Three-parted. Stigma color: Close to 145B. Style color: Close to 145B. Ovary color: Close to 144A.

*Seed/fruit.*—Seed and fruit development have not been observed.

Disease/pest resistance: Plants of the *Phlox* have not been observed to be resistant to pathogens and pests common to *Phlox*.

Garden performance: Plants of the new *Phlox* have been observed to have good garden performance and to tolerate rain, wind and temperatures ranging from about 0° C. to about 35° C.

It is claimed:

1. A new and distinct *Phlox* plant named 'Sunphlocopapi' as illustrated and described.

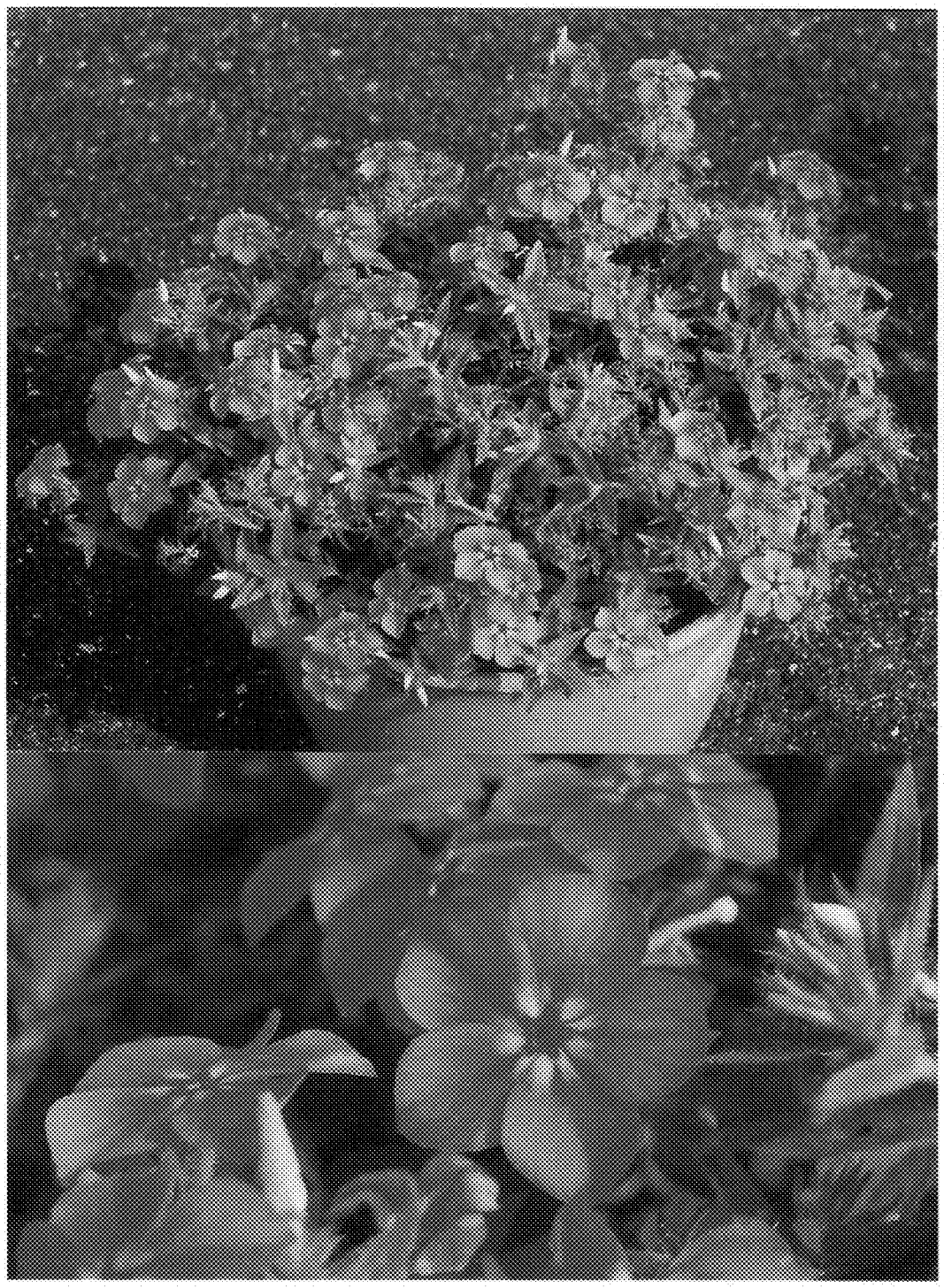

* * * * *